US006718206B2

(12) United States Patent
Casavant (10) Patent No.: US 6,718,206 B2
(45) Date of Patent: Apr. 6, 2004

(54) PERMANENT ATRIAL-HIS-VENTRICULAR SEQUENTIAL PACING (75) Inventor: David A. Casavant, Reading, MA (US)

(73) Assignee: Medtronic, Inc., Minneapolis, MN (US)

(*) Notice: Subject to any disclaimer, the term of this patent is extended or adjusted under 35 U.S.C. 154(b) by 258 days.

(21) Appl. No.: 10/047,632

(22) Filed: Oct. 23, 2001

(65) Prior Publication Data

US 2003/0078625 A1 Apr. 24, 2003

(51) Int. Cl.$^7$ ............................................. A61N 1/362
(52) U.S. Cl. .................................................. 607/9
(58) Field of Search .............................. 607/9, 14, 15, 607/18, 25

(56) References Cited

U.S. PATENT DOCUMENTS

| 4,354,497 A | 10/1982 | Kahn ..................... 128/419 D |
| 5,083,564 A | 1/1992 | Scherlag ................ 128/419 PG |
| 5,174,289 A | 12/1992 | Cohen ................... 128/419 PG |
| 5,246,014 A | 9/1993 | Williams et al. ............ 607/122 |
| 5,320,642 A | 6/1994 | Scherlag ........................ 607/9 |
| 5,403,356 A | 4/1995 | Hill et al. ...................... 607/14 |
| 5,514,163 A | 5/1996 | Markowitz et al. ............ 607/9 |
| 5,601,614 A | 2/1997 | Ekwall ........................ 607/25 |
| 5,643,338 A | 7/1997 | Bornzin et al. .............. 607/123 |
| 6,493,586 B1 | 12/2002 | Stahmann et al. ............ 607/27 |
| 6,609,027 B2 * | 8/2003 | Kroll et al. .................... 607/9 |
| 2002/0120318 A1 | 8/2002 | Kroll et al. ................. 607/149 |

FOREIGN PATENT DOCUMENTS

EP  1 234 597 A2  8/2002  .......... A61N/1/368

OTHER PUBLICATIONS

Adomian et al., "Myofibrillar Disarray Produced in Normal Hearts by Chronic Electrical Pacing," *Am. Heart J.*, vol. 112, No. 1, p. 79–83 (Jul. 1986).

Baller, D. et al., "Comparison of the effects of right atrial, right ventricular apex and atrioventricular sequential pacing on myocardial oxygen consumption and cardiac efficiency: A laboratory investigation," *PACE*, vol. 11, p. 394–403 (Apr. 1988).

Brecker et al., "Effects of Dual–Chamber Pacing with Short Atrioventricular Delay in Dilated Cardiomyopathy," *Lancet*, vol. 340, p. 1308–12 (Nov. 28, 1992).

Deshmukh et al., Permanent, Direct His–Bundle Pacing—A Novel Approach to Cardiac Pacing in Patients with Normal His–Purkinje Activation, *Circulation*, p. 869–77 (Feb. 29, 2000).

Gomes et al., "Ventricular Septal Motion and Left Ventricular Dimensions During Abnormal Ventricular Activation," *The American J. of Cardiology*, vol. 39, p. 641–50 (May 4, 1977).

(List continued on next page.)

*Primary Examiner*—Carl Layno
(74) *Attorney, Agent, or Firm*—Girma Wolde-Michael; Elisabeth L. Belden (57) ABSTRACT A method and apparatus for cardiac pacing and, more particularly, for Atrial-His-Ventricular sequential pacing to improve sino-atrial node dysfunction or heart block superior to the His bundle. As a derivative, His-Ventricular sequential pacing can be employed to treat permanent atrial fibrillation.

7 Claims, 5 Drawing Sheets

OTHER PUBLICATIONS

Gregoratos, G. et al., "ACC/AHA guidelines for implantation of cardiac pacemakers and antiarrhythmic devices: Executive summary," *Circulation*, vol. 97, p. 1325–1335 (1998).

Hochleitner et al., "Usefulness of Physiologic Dual–Chamber Pacing in Drug–Resistant Idiopathic Dilated Cardiomyopathy," *Am. J. of Cardiology*, vol. 66, No. 2, p. 198–202 (Jul. 15, 1990).

Karpawich et al., "Altered Cardiac Histology Following Apical Right Ventricular Pacing in Patients with Congenital Atrioventricular Block," *PACE*, vol. 22, p. 1372–77 (Sep. 1999).

Karpawich et al., "Comparative Left Ventricular Function Following Atrial, Septal and Apical Single Chamber Heart Pacing in the Young," *PACE*, vol. 20, p. 1983–88, Part I (Aug. 1997).

Karpawich et al., "Developmental Sequelae of Fixed–Rate Ventricular Pacing in the Immature Canine Heart: An Electrophysiologic, Hemodynamic, and Histopathologic Evaluation," *American Heart Journal*, vol. 119, No. 5, p. 1077–83 (May 1990).

Kay et al., "The Ablate and Pace Trial: A Prospective Study of Catheter Ablation of the AV Conduction System and Permanent Pacemaker Implantation for Treatment of Atrial Fibrillation," *J. of Interventional Cardiac Electrophysiology*, vol. 2, p. 121–135 (1998).

Lee et al., "Effects of Long–Term Right Ventricular Apical Pacing on Left Ventricular Perfusion, Innervation, Function and Histology," *JACC*, vol. 24, No. 1, P. 225–32 (Jul. 1994).

Prinzen et al., "Asymmetric Thickness of the Left Ventricular Wall Resulting from Asynchronous Electric Activation: A Study in Dogs with Ventricular Pacing and in Patients with Left Bundle Branch Block," *American Heart Journal*, vol. 130, No. 5, p. 1045–53 (Nov. 1995).

Tse et al., "Long–Term Effect of Right Ventricular Pacing on Myocardial Perfusion and Function," *JACC*, vol. 29, No. 4, p. 744–9 (Mar. 15, 1997).

Twidale et al., "Comparison of the Effects of AV Nodal Ablation Versus AV Nodal Modification in Patients with Congestive Heart Failure and Uncontrolled Atrial Fibrillation," *PACE*, vol. 21, p. 641–651, Part I (Apr. 1998).

Vanderheyden et al., "Hemodynamic Deterioration Following Radiofrequency Ablation of the Atrioventricular Conduction System," *PACE*, vol. 20, p. 2422–28, Part I (Oct. 1997).

* cited by examiner

PERMANENT ATRIAL-HIS-VENTRICULAR SEQUENTIAL PACING

FIELD OF THE INVENTION

The present invention relates to a method and apparatus for cardiac pacing and, more particularly, for Atrial-His-Ventricular sequential pacing to improve sinoatrial node dysfunction or heart block superior to the His bundle. As a derivative, His-Ventricular sequential pacing can be employed to treat permanent atrial fibrillation.

BACKGROUND OF THE INVENTION

The sinoatrial (SA) node represents the natural pacemaker that controls the rhythmic electrical excitation in a normal human heart. At an appropriate time, an electrical impulse arising from the SA node is transmitted to the right and left atrial chambers. This impulse causes muscle tissue surrounding the atrium to depolarize and contract which generates an electrical signal known as a P-wave. The same electrical impulse arising from the SA node also travels to the right and left ventricles through the atrioventricular (AV) node and atrioventricular (AV) bundle. The AV node, situated in the lower portion of the right atrium, receives the impulse to contract. The impulse is then transmitted through the AV bundle comprising Common Bundle of His (His bundle), right and left bundle branches, and Purkinje fibers that cover most of the endocardial surface of the ventricles. The ventricular muscle tissue depolarizes, generating an R-wave, then contracts. This forces blood held in the ventricles through the arteries and to various body locations. This action is repeated in a rhythmic cycle in which the atrial and ventricular chambers alternately contract and pump, then relax and fill.

Disturbances of impulse formation by the sinus node and/or AV conduction block due to disease and aging are commonly treated by artificial pacing. An artificial pacemaker is an implantable medical device that monitors the activity of the heart for the occurrence of P- and/or R-waves. When a P- or R-wave is not sensed after a prescribed period of time, the pacemaker electronically generates stimuli in order to force the depolarization of the atria and/or ventricles. A pacemaker-generated stimulus that is delivered to the atria is known as an A-pulse, whereas a stimulus delivered to the ventricles is a V-pulse.

Different methods of artificial pacing have been employed including single or bi-ventricular pacing and dual chamber pacing. In single ventricular pacing, a pacing lead connected to an electrode is typically implanted in the apex of the right ventricle to deliver electrical impulses to the ventricular muscle tissue. However, this type of pacing results in the loss of synchronous mechanical contraction of the right and left ventricles due to the interventricular delay in impulse propagation to the left ventricle. This results in an immediate decrease in cardiac output along with potential deterioration of ventricular function over the long term as permanent changes occur in myocardial perfusion and structure. A method to pace both ventricles, bi-ventricular pacing, has been demonstrated to restore substantially simultaneous contraction of both ventricles and is accomplished by placing one pacing lead in the apex of the right ventricle and another pacing lead through the coronary sinus into a vein on the left ventricular wall. The surgical procedure used to implant the pacing lead in the coronary sinus however may be complex and a long pacing lead is needed to connect the electrode to the pulse generator thus requiring a higher voltage resulting in a large drain on the power source generating the pulses. In dual chamber pacing (DDD/R), electrodes connected to pacing leads are placed in the atria (for example the right atrium) and one or both of the ventricles. Under this method, ventricular synchrony can be achieved when electrodes are placed in both ventricles and an optimal delay between the A pulse and V pulse (AV delay) is utilized. However, this still does not produce a similarly coordinated contraction as compared to natural AV bundle activation.

Patients with SA node dysfunction or heart block superior to the His bundle, due to their conditions, suffer from a delay in the electrical response from the atria to the ventricles. According to current practice, patients with these conditions typically receive a DDD/R pacemaker. Many of these patients however still have normal ventricular contraction and thus are unnecessarily ventricularly paced due to pacemaker programming restrictions and/or prolonged AV conduction times. Because of this unnecessary ventricular pacing, these patients experience a decrease in cardiac efficiency due to the uncoordinated contraction sequence and eventually exhibit adverse long-term effects. Therefore, it's desired to develop a pacing system for these patients, that is more tailored to their cardiac condition, without utilizing ventricular pacing means.

It has recently been shown in U.S. Pat. No. 5,320,642 (Scherlag) that a pacing lead can be implanted near the His bundle, just below the AV node to pace the ventricles as an alternative to ventricular pacing. When the ventricles are paced through this natural conduction system, the ventricles contract in a more coordinated fashion as compared to pacing the ventricles themselves thus improving cardiac output. Also, patients receiving ventricular pacing who do not need to be ventricularly paced are spared from the long term harmful hemodynamic effects that occur from continuous ventricular pacing. However, there is a risk that the electrode may become dislodged from the His bundle or that the patient may subsequently experience heart block inferior to the His bundle. Therefore, it's desired to utilize this more natural His bundle pacing system in order to obtain a more coordinated contraction sequence, yet retain the option to ventricularly pace should the His bundle pacing lead fail or heart block below the His bundle occur.

SUMMARY OF THE INVENTION

The present invention is directed to a pacing apparatus and method for sequentially pacing the atria, His bundle and ventricles to provide synchronous mechanical contractions to improve cardiac output and prevent long term hemodynamic effects caused by unnecessary ventricular pacing. The pacing apparatus includes pacing leads extending from a pacer that lead to prescribed positions in the atria, AV septum and ventricle of the heart. The pacing leads have electrodes attached to their distal ends for measuring and delivering electrical impulses. The pacing leads leading to the atria and ventricles are programmed to deliver electrical pulses, on a demand mode basis, if natural electrical signals are not measured within a predetermined period of time. The pacing lead leading to the AV septum delivers continuous electrical pulses to the His bundle immediately following the sensing of atrial activity. These electrical pulses then travel through the right and left bundle branches and to the Purkinje fibers causing the ventricles to depolarize and contract. By utilizing this natural conduction system, the ventricles contract in a more coordinated manner as compared to ventricular pacing thus improving cardiac output and performance.

In one embodiment of the present invention, the pacing apparatus is provided for patients who suffer from sino-atrial (SA) node dysfunction or heart block superior to the His bundle. Because these patients typically have normal ventricular contraction, continuously pacing the His bundle results in electrical pulses being sent from the atria to the ventricles to travel more quickly thus allowing the ventricular pacing lead to remain dormant during the pacing cycle. The ventricular pacing is provided only for emergency situations such as, for example, inter alia, if the His bundle pacing lead should fail or if heart block inferior to the His bundle should occur.

In another embodiment of the present invention, the pacing apparatus is provided for patients who suffer from permanent atrial fibrillation. The His bundle pacing lead is implanted following AV node ablation to provide electrical pulses to the ventricles causing depolarization and contraction. Again, a ventricular pacing lead is provided but remains dormant and is activated only in emergency situations.

DETAILED DESCRIPTION OF THE PREFERRED EMBODIMENT

The following description is of the best mode presently contemplated for carrying out the invention. This description is not to be taken in a limiting sense, but is made merely for the purpose of describing the general principles of the invention.

Figure 1:
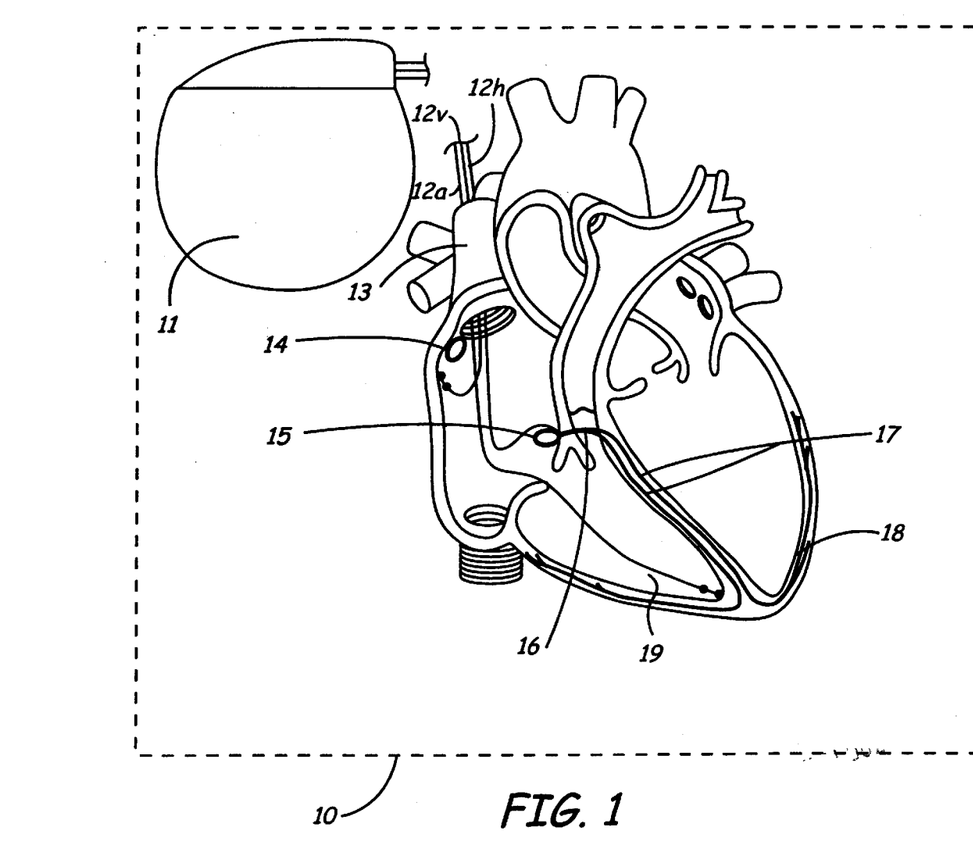
FIG. 1 is a schematic representation of one embodiment of the pacing system in accordance with this invention whereby pacing leads are provided, the leads being shown with electrodes positioned in the heart.

Referring to FIG. 1, there is shown a schematic representation of a pacing system 10 in accordance with one embodiment of the present invention. The pacing system 10 comprises an implantable pacemaker (pacer) 11, from which three leads, 12A (atrial), 12H (AV bundle) and 12V (ventricle) extend. It is recognized that actual lead packaging may vary, but at least three functional conductive leads must originate in pacer 11 to direct energy to various locations in the cardiac tissue. The pacing leads 12A, 12H and 12V, in this embodiment, enter the heart through the superior vena cava 13. Each pacing lead provides electrodes at or proximate to their distal ends for pacing and sensing electrical stimuli. A plurality of electrodes can be placed at the distal ends of each lead for measuring and delivering pulses, however for simplicity it's assumed each lead has one electrode for the following discussion. Pacing lead 12A is anchored or otherwise positioned generally in the right atrium just below the SA node 14 for contacting the right atrium. Pacing lead 12H is positioned distal to the blocked or slowly conducting AV node and in the AV septum 15 for contacting the AV bundle comprising His bundle 16, right and left bundle branches 17, and the Purkinje fibers 18. The His bundle 16 is a structure of cardiac muscle through which all impulses from the atria are conducted to the ventricles of the heart. Pacing lead 12V is positioned so that its distal end is anchored in the apex of the right ventricle 19. The electrodes are stabilized or fixed in their respective positions in a manner well known in the art.

Figure 2:
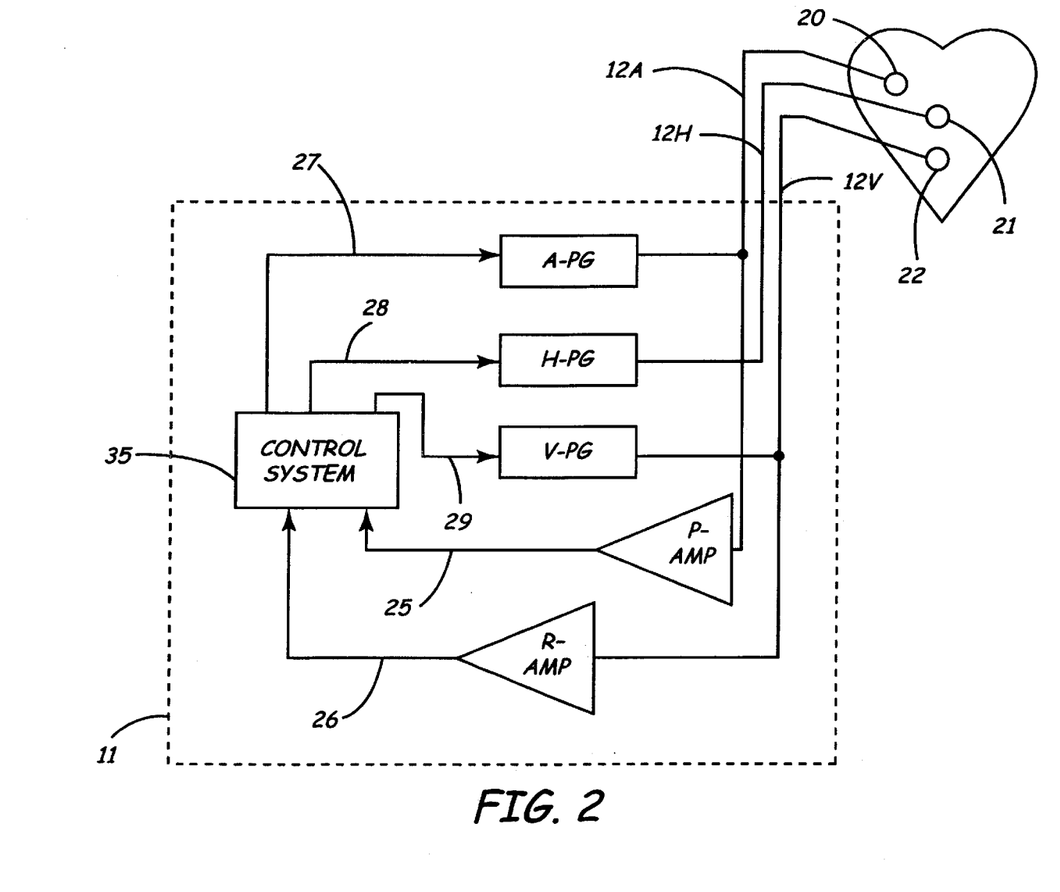
FIG. 2 is a block diagram of one embodiment of the implantable pacemaker system.

Referring then to FIG. 2, a block diagram of pacer 11 is illustrated. The pacer is adapted to interface with the atria, His bundle and ventricles of the heart. Those portions of pacer 11 that interface with the atria, His bundle and ventricles, and the corresponding portions of control system 35 are commonly referred to as the atrial, His bundle and ventricular channels, respectively.

Pacer 11 generates electrical pulses that are transmitted through pacing leads 12A, 12H and 12V. Control system 35 controls pacer 11. The control system includes timing circuitry and a microprocessor for carrying out logical steps in analyzing received signals, and determining when pace pulses should be initiated, with particular sequences and locations comprising part of the present invention. The leads 12A, 12H, and 12V carry the stimulating pulses to electrodes 20, 21 and 22 from an atrial pulse generator A-PG, His bundle pulse generator H-PG and a ventricular pulse generator V-PG 27, respectively. An electrical pulse generated by A-PG is known as an A-pulse; an electrical pulse generated by H-PG is known as an H-pulse; and an electrical pulse generated by V-PG is known as a V-pulse. Further, natural electrical signals from the atria (P-waves) are carried from the electrode 20, through lead 12A, to the input channel of an atrial channel sense amplifier P-AMP. Likewise, natural electrical signals from the ventricles (R-waves) are carried from electrode 22, through the lead 12V, to the input terminal of a ventricular sense channel amplifier R-AMP. Thus, when a P-wave or R-wave is generated by the heart, it is sensed by electrodes 20 or 22 and amplified by P-AMP or R-AMP. The control system 35 receives the output signals from P-AMP over signal line 25. The control system 35 also receives the output signals from R-AMP over signal line 26. The control system 35 also generates trigger signals when needed that are sent to A-PG, H-PG and V-PG over signal lines 27, 28 and 29 respectively. These trigger signals are generated each time that an electrical pulse is to be generated by the respective pulse generator.

Figure 3:
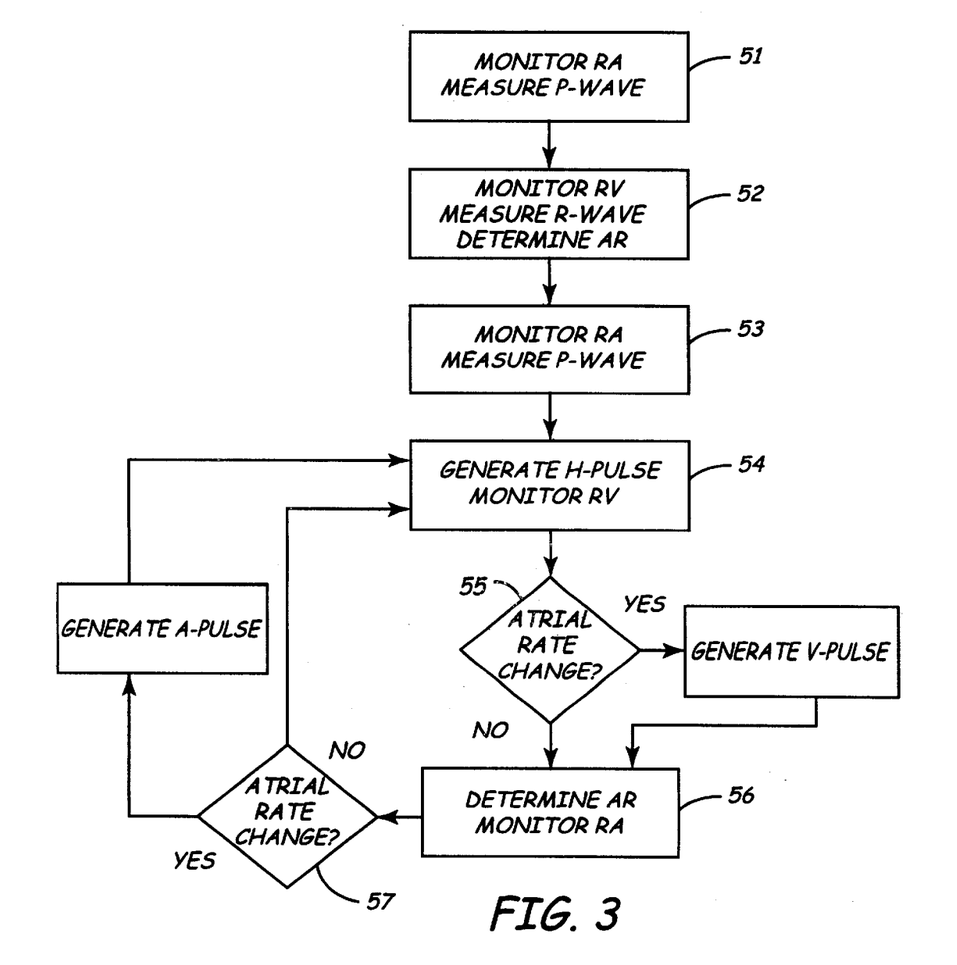
FIG. 3 is a logic control diagram for pacing patients suffering from sinoatrial node dysfunction or superior His bundle heart block.

Referring now to FIG. 3, there is shown a logic control flow diagram for controlling the system of this invention to pace a patient with SA node dysfunction or AV conduction block superior to the His bundle. The assumption is that the right and left ventricles are functioning normally but that sinus signals from the SA node to the AV Bundle are not occurring or are being delayed from the atria to the ventricles within the AV node. As shown at 51, the pacer monitors the right atrium and measures a P-wave generated by the SA node. As shown in 54, once a P-wave is sensed, the pacer transmits an H-pulse through the pacing lead to an electrode located distal to the AV node to stimulate the His bundle. The H-pulse is transmitted through the His bundle to the right and left bundle branches of the heart and then to the Purkinje fibers to cause ventricular depolarization. Then, the pacer senses the right ventricle for an R-wave. As shown in 55, if an R-wave is not sensed following atrial activity plus some predescribed period of time, the right ventricle is electrically paced with a V-pulse generated by the pacer. In 56, a subsequent P-wave is sensed in the right atrium. As shown in 57, if a P-wave is not sensed following ventricular activity plus some prescribed period of time, the pacer generates an electrical stimulus, or A-pulse, to the right atrium. An H-pulse is generated immediately following atrial activity and sent to the electrode located near the AV bundle and the right ventricle is again monitored for ventricular depolarization as the cardiac cycle continues. The advantage to this system is that both the atrial and ventricular pacing leads remain dormant throughout the cardiac cycle unless a P-wave or R-wave is not sensed within a prescribed period of time. This eliminates the harmful hemodynamic effects suffered by patients who are currently unnecessarily ventricularly paced. In addition, using the natural conduction system of the SA node, the His-bundle, right and left bundle branches and Purkinje fibers as a pacing pathway generates a more natural synchronous mechanical ventricular contraction to improve cardiac output.

Figure 4:
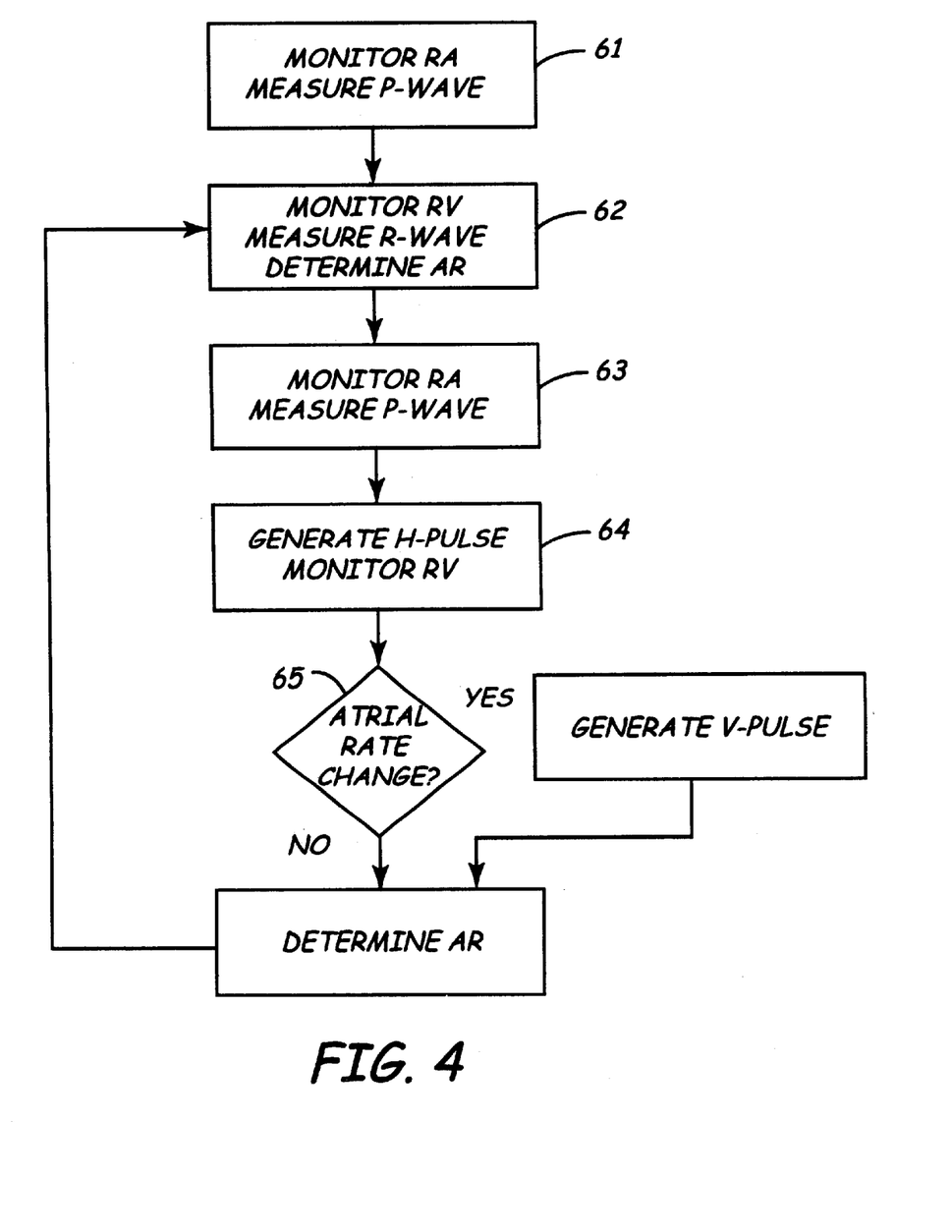
FIG. 4 is a logic control diagram for pacing patients suffering from heart block at the AV node.

In another embodiment of the invention, shown in logic control flow diagram FIG. 4, it's assumed that the patient suffers only from heart block located in the AV node. In 61, the pacer measures a P-wave generated by the SA node. To increase conduction time from the SA node to the ventricles, an electrode is placed distal to the AV node to stimulate the His bundle. Then, in 64, the pacer sends an H-pulse to this electrode immediately following the sensing of a P-wave. As shown in 65, the ventricular pacing lead remains dormant throughout this cycle unless an R-wave is not sensed following atrial activity plus a prescribed period of time, after which the pacer would generate a V-pulse to force the ventricles to contract.

Figure 5:
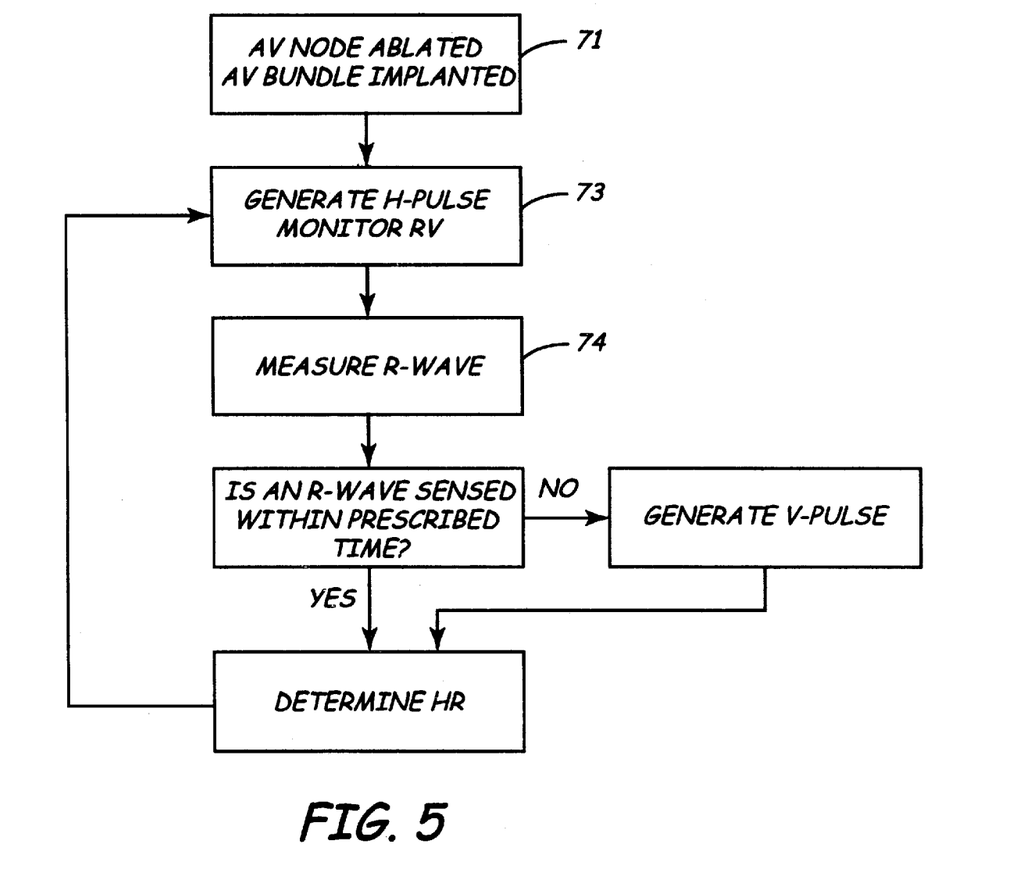
FIG. 5 is a logic control diagram for pacing patients suffering from permanent atrial fibrillation.

Referring to FIG. 5, there is shown a logic control flow diagram for controlling the system of this invention to pace a patient with permanent atrial fibrillation. It's assumed that the patient suffers from a fast and unreliable ventricular response. According to current practice, these patients are treated by ablating the AV node and placing a permanent single-chamber pacemaker with the lead tip in the right ventricle to restore normal ventricular rhythm. However, this can cause hemodynamic deterioration and death in some patients. In order to provide these patients with improved long-term pacing, AV node ablation can be followed by permanent His bundle pacing. As shown in 71, AV node ablation is preceded by implanting a pacemaker distal to the AV node to stimulate the His bundle. Continuous H-pulses are transmitted to the His bundle via the electrode located at the AV bundle, to cause the ventricles to depolarize as shown in 73 and 74. Because there is a risk that the AV bundle lead could become dislodged or that the patient could suffer heart block inferior to the AV bundle lead, a second pacing lead is anchored in the apex of the right ventricle to provide V-pulses when necessary. As shown, if an R-wave is not sensed within a prescribed time following an H-pulse, a V-pulse is generated by the pacer and transmitted to the right ventricle causing the ventricles to contract. The subsequent H-pulse is generated according to the operating pacing rate to continue the cardiac cycle. Thus, a V-pulse is generated only on an emergency basis, i.e. when heart block occurs inferior to the His bundle.

While the invention herein disclosed has been described by means of specific embodiments and applications thereof, numerous modifications and variations could be made thereto by those skilled in the art without departing from the scope of the invention set forth in the claims.

What is claimed is:

1. A method of providing atrial-ventricular (AV) synchronous pacing to a heart through a dual chamber pacemaker pulse generator coupled with pacing leads extending to ventricular pace/sense electrodes disposed in operative relation to a ventricle, atrial pace/sense electrodes disposed in operative relation to an atrium, and His bundle pace electrodes disposed along the AV septum in operative relation to the bundle of His comprising the steps of:

determining the intrinsic AR interval of the patient's heart by:
sensing at least one P-wave associated with depolarization of an atrium through the atrial pace/sense electrodes as an atrial sensed event;
sensing at least one R-waves associated with depolarizations of a ventricle through the ventricular pace/sense electrodes as a ventricular sensed event; and
timing an intrinsic AR interval from at least one pair of successive atrial and ventricular sensed events;

establishing an A-H delay as a function of the determined intrinsic AR interval;

establishing an AV delay that is shorter than the determined intrinsic AR interval; and synchronously pacing the patient's heart by:
establishing an atrial pacing escape interval;
timing out the atrial pacing escape interval;
sensing P-waves associated with depolarizations of the atrium through the atrial pace/sense electrodes as atrial sensed events;
restarting the atrial pacing escape interval on the sensing of an atrial sensed event within said atrial pacing escape interval;
delivering an atrial pace pulse through the atrial pace/sense electrodes to the atrium at the time out of the atrial pacing escape interval;
timing out the A-H delay from an atrial sensed event or delivery of an atrial pace pulse;
delivering a His bundle pacing pulse through the His bundle pace electrodes to the bundle of His upon time-out of the A-H delay;
timing out the AV delay from an atrial sensed event or delivery of an atrial pace pulse;
sensing R-waves associated with depolarizations of the ventricle through the ventricular pace/sense electrodes as ventricular sensed events;
halting the time-out of the AV delay upon a ventricular sensed event occurring during time-out of the AV delay; and
delivering a ventricular pacing pulse through the ventricular pace/sense electrodes upon time-out of the AV delay;

wherein the step of establishing an A-H delay as a function of the determined intrinsic AR interval comprises setting the A-H delay to be shorter than the AV delay.

2. A method of providing atrial-ventricular (AV) synchronous pacing to a heart through a dual chamber pacemaker pulse generator coupled with pacing leads extending to ventricular pace/sense electrodes disposed in operative relation to a ventricle, atrial pace/sense electrodes disposed in operative relation to an atrium, and His bundle pace electrodes disposed along the AV septum in operative relation to the bundle of His comprising the steps of:

determining the intrinsic AR interval of the patients heart by:
sensing at least one P-wave associated with depolarization of an atrium through the atrial pace/sense electrodes as an atrial sensed event;
sensing at least one R-wave associated with depolarizations of a ventricle through the ventricular pace/sense electrodes as a ventricular sensed event; and
timing an intrinsic AR interval from at least one air of successive atrial and ventricular sensed events;

establishing an A-H delay as a function of the determined intrinsic AR interval; and synchronously pacing the patient's heart by:
  establishing an atrial pacing escape interval;
  timing out the atrial pacing escape interval;
  sensing P-waves associated with depolarizations of the atrium through the atrial pace/sense electrodes as atrial sensed events;
  restarting the atrial pacing escape interval on the sensing of an atrial sensed event within said atrial pacing escape interval;
  delivering an atrial pace pulse through the atrial pace/sense electrodes to the atrium at the time out of the atrial pacing escape interval;
  timing out the A-H delay from an atrial sensed event or delivery of an atrial pace pulse; and
  delivering a His bundle pacing pulse through the His bundle pace electrodes to the bundle of His upon time-out of the A-H delay;
wherein the step of establishing an A-H delay as a function of the determined intrinsic AR interval comprises setting the A-H delay to be shorter than the determined intrinsic AR interval.

3. A method of providing atrial-ventricular (AV) synchronous pacing to a heart through a dual chamber pacemaker pulse generator coupled with pacing leads extending to ventricular pace/sense electrodes disposed in operative relation to a ventricle atrial pace/sense electrodes disposed in operative relation to an atrium, and His bundle pace electrodes disposed along the AV septum in operative relation to the bundle of His comprising the steps of:
  determining the intrinsic AR interval of the patient's heart by:
    sensing at least one P-wave associated with depolarization of an atrium through the atrial pacelsense electrodes as an atrial sensed event;
    sensing at least one R-wave associated with depolarizations of a ventricle through the ventricular pace/sense electrodes as a ventricular sensed event; and
    timing an intrinsic AR interval from at least one pair of successive atrial and ventricular sensed events:
  establishing an A-H delay as a function of the determined intrinsic AR interval; and
  synchronously pacing the patient's heart by:
    establishing an atrial pacing escape interval;
    timing out the atrial pacing escape interval;
    sensing P-waves associated with depolarizations of the atrium through the atrial pace/sense electrodes as atrial sensed events;
    restarting the atrial pacing escape interval on the sensing of an atrial sensed event within said atrial pacing escape interval;
    delivering an atrial pace pulse through the atrial pace/sense electrodes to the atrium at the time out of the atrial pacing escape interval;
    timing out the A-H delay from an atrial sensed event or delivery of an atrial pace pulse; and
    delivering a His bundle pacing pulse through the His bundle pace electrodes to the bundle of His upon time-out of the A-H delay;
  wherein the step of establishing an A-H delay as a function of the determined intrinsic AR interval comprising setting the A-H delay to be longer than the determined intrinsic AR interval.

4. An atrial-ventricular (AV) synchronous pacing system that comprises a dual chamber pacemaker pulse generator coupled with pacing leads extending to ventricular pace/sense electrodes disposed in operative relation to a ventricle, atrial pace/sense electrodes disposed in operative relation to an atrium, and His bundle pace electrodes disposed along the AV septum in operative relation to the bundle of His, the pulse generator further comprising:
  means for establishig an atrial pacing escape interval;
  means for timing out the atrial pacing escape interval;
  means for sensing P-waves associated with depolarizations of the atrium through the atrial pace/sense electrodes as atrial sensed events;
  means for restarting the atrial pacing escape interval on the sensing of an atrial sensed event within said atrial pacing escape interval;
  means for delivering an atrial pace pulse through the atrial pace/sense electrodes to the atrium at the time out of the atrial pacing escape interval;
  means for timing out an A-H delay from an atrial sensed event or delivery of an atrial pace pulse;
  means for delivering a His bundle pacing pulse through the His bundle pace electrodes to the bundle of His upon time-out of the A-H delay;
  means for determining the intrinsic AR interval of the patients heart by:
    sensing at least one P-wave associated with depolarization of an atrium through the atrial pace/sense electrodes as an atrial sensed event;
    sensing at least one R-waves associated with depolarizations of a ventricle through the ventricular pace/sense electrodes as a ventricular sensed event; and
    timing an intrinsic AR interval from at least one pair of successive atrial and ventricular sensed events; and
  means for establishing the A-H delay as a function of the determined intrinsic AR interval;
  wherein the means for establishing an A-H delay as a function of the determined intrinsic AR interval comprises means for setting the A-H delay to be shorter than the determined intrinsic AR interval.

5. An atrial-ventricular (AV) synchronous pacing system that comprises a dual chamber pacemaker pulse generator coupled with pacing leads extending to ventricular pace/sense electrodes disposed in operative relation to a ventricle, atrial pace/sense electrodes disposed in operative relation to an atrium, and His bundle pace electrodes disposed along the AV septum in operative relation to the bundle of His, the pulse generator further comprising:
  means for establishig an atrial pacing escape interval;
  means for timing out the atrial pacing escape interval;
  means for sensing P-waves associated with depolarizations of the atrium through the atrial pace/sense electrodes as atrial sensed events;
  means for restarting the atrial pacing escape interval on the sensing of an atrial sensed event within said atrial pacing escape interval;
  means for delivering an atrial pace pulse through the atrial pace/sense electrodes to the atrium at the time out of the atrial pacing escape interval;
  means for timing out an A-H delay from an atrial sensed event or delivery of an atrial pace pulse;
  means for delivering a His bundle pacing pulse through the His bundle pace electrodes to the bundle of His upon time-out of the A-H delay;
  means for determining the intrinsic AR interval of the patient's heart by:
    sensing at least one P-wave associated with depolarization of an atrium through the atrial pace/sense electrodes as an atrial sensed event;

sensing at least one R-waves associated with depolarizations of a ventricle through the ventricular pace/sense electrodes as a ventricular sensed event; and timing an intrinsic AR interval from at least one pair of successive atrial and ventricular sensed events; and means for establishing the A-H delay as a function of the determined intrinsic AR interval;

wherein the means for establishing an A-H delay as a function of the determined intrinsic AR interval comprises means for setting the A-H delay to be longer than the determined intrinsic AR interval.

6. A pacemaker configured to by-pass sino-atrial node dysfunction or heart block superior to a His bundle comprising:

an atrial electrode adapted to sense atrial electrical activity;

a His bundle electrode in contact with the His bundle and adapted to deliver stimulating pulses to the His bundle;

a ventricular electrode in contact with a ventricle of a heart and adapted to sense ventricular electrical activity and to deliver a stimulating pulse to the ventricle; and a pulse generator coupled to the atrial electrode, the HIS bundle electrode and the ventricular electrode, the generator adapted to process sensed electrical activity and generate His stimulation pulses causing ventricular depolarization after the atrial electrical activity is sensed; whereby a ventricular pulse is generated by the pulse generator and delivered to the ventricle if ventricular depolarization is not sensed by the ventricular electrode within a prescribed time from the sensed atrial electrical activity.

7. The pacemaker of claim 6, wherein the atrial electrode is further adapted to deliver stimulating pulses to the right atrium and the pulse generator is further adapted to generate the atrial electrical activity via the atrial electrode.

* * * * *

UNITED STATES PATENT AND TRADEMARK OFFICE
CERTIFICATE OF CORRECTION

PATENT NO. : 6,718,206 B2
DATED : April 6, 2004
INVENTOR(S) : David A. Casavant

It is certified that error appears in the above-identified patent and that said Letters Patent is hereby corrected as shown below:

Column 6,
Line 56, delete "the patients", replace with -- the patient's --.
Line 64, delete "one air", replace with -- one pair --.

Column 7,
Line 26, delete "a ventricle atrial", replace with -- a ventricle, atrial --.

Column 8,
Line 23, delete "the patients", replace with -- the patient's --.

Signed and Sealed this

Eighteenth Day of January, 2005

JON W. DUDAS
*Director of the United States Patent and Trademark Office*